(12) United States Patent
Kellerman et al.

(10) Patent No.: US 12,121,235 B1
(45) Date of Patent: Oct. 22, 2024

(54) PERCUTANEOUS ANASTOMOTIC DEVICE USED TO CREATE A NATIVE VESSEL BYPASS

(71) Applicant: Avenu Medical, Inc., San Juan Capistrano, CA (US)

(72) Inventors: Brad M. Kellerman, Escondido, CA (US); Justin K. Mann, Lake Elsinore, CA (US)

(73) Assignee: Avenu Medical, Inc., San Juan Capistrano, CA (US)

( * ) Notice: Subject to any disclaimer, the term of this patent is extended or adjusted under 35 U.S.C. 154(b) by 438 days.

(21) Appl. No.: 17/122,914

(22) Filed: Dec. 15, 2020

Related U.S. Application Data

(60) Provisional application No. 63/039,681, filed on Jun. 16, 2020, provisional application No. 62/948,689, filed on Dec. 16, 2019.

(51) Int. Cl.
  *A61B 17/11* (2006.01)
  *A61B 17/00* (2006.01)
  (Continued)

(52) U.S. Cl.
  CPC .............. *A61B 17/11* (2013.01); *A61B 18/04* (2013.01); *A61B 2017/00238* (2013.01);
  (Continued)

(58) Field of Classification Search
  CPC ................ A61B 17/11; A61B 17/3403; A61B 17/12109; A61B 17/12045; A61B 17/3417; A61B 17/12036; A61B 17/12031; A61B 17/1214; A61B 2017/1107; A61B 2017/00238; A61B 2017/00252; A61B 2017/00243; A61B 2017/00247; A61B 2017/12127; A61B 2017/22097; A61B 2017/22067; A61B 2017/1139; A61B 2017/00783; A61B 2017/3454; A61B 2018/00577; A61B 2018/00392; A61B 2018/1425; A61B 2018/00369; A61B 2018/00404; A61B 2018/00619; A61B 18/1492; A61B 18/1477; A61B 18/245; A61B 18/04; A61M 25/09
  See application file for complete search history.

(56) References Cited

U.S. PATENT DOCUMENTS

| | | | | |
|---|---|---|---|---|
| 5,846,241 A | * | 12/1998 | Kittur | A61B 18/1492 606/50 |
| 6,190,353 B1 | * | 2/2001 | Makower | A61B 17/12131 600/137 |

(Continued)

*Primary Examiner* — Khadijeh A Vahdat
*Assistant Examiner* — Marina Delaney Templeton
(74) *Attorney, Agent, or Firm* — Stinson LLP

(57) ABSTRACT

A method of creating a native vessel bypass percutaneously includes steps of selecting a target procedural site adjacent to a paired artery and vein, usually near an occlusion or blockage disposed in the artery and advancing a catheter through the vein with its distal tip extending through the vessel walls into the adjacent artery. An anastomosis is formed by applying heat to tissue forming the vessel walls which is captured between surfaces on a proximal base and the distal tip of the catheter. The venous valves are disabled to permit retrograde venous flow of arterial blood, in order to bypass the arterial occlusion.

17 Claims, 20 Drawing Sheets

(51) Int. Cl.
*A61B 17/34* (2006.01)
*A61B 18/00* (2006.01)
*A61B 18/04* (2006.01)
*A61M 25/09* (2006.01)

(52) U.S. Cl.
CPC ............... *A61B 2017/00783* (2013.01); *A61B 2017/1107* (2013.01); *A61B 17/3403* (2013.01); *A61B 2017/3454* (2013.01); *A61B 2018/00404* (2013.01); *A61B 2018/00577* (2013.01); *A61B 2018/00619* (2013.01); *A61M 25/09* (2013.01)

(56) References Cited

U.S. PATENT DOCUMENTS

| | | | |
|---|---|---|---|
| 6,579,311 B1 * | 6/2003 | Makower | A61B 17/12022 606/8 |
| 6,726,677 B1 * | 4/2004 | Flaherty | A61B 17/3417 604/528 |
| 9,439,710 B2 | 9/2016 | Reu et al. | |
| 9,452,015 B2 | 9/2016 | Kellerman et al. | |
| 9,474,562 B2 | 10/2016 | Kellerman et al. | |
| 10,772,672 B2 | 9/2020 | Hull et al. | |
| 11,197,979 B2 * | 12/2021 | Crisco | A61M 25/0194 |
| 2013/0281998 A1 * | 10/2013 | Kellerman | A61B 18/082 606/29 |
| 2014/0142561 A1 * | 5/2014 | Reu | A61B 18/082 606/29 |
| 2015/0366580 A1 * | 12/2015 | Lenihan | A61B 17/3403 604/8 |
| 2016/0045219 A1 * | 2/2016 | Guala | A61B 17/22 606/185 |
| 2017/0202603 A1 * | 7/2017 | Cohn | A61F 2/2475 |

* cited by examiner

Figure 8: Image showing valve elimination with Ellipsys like device.

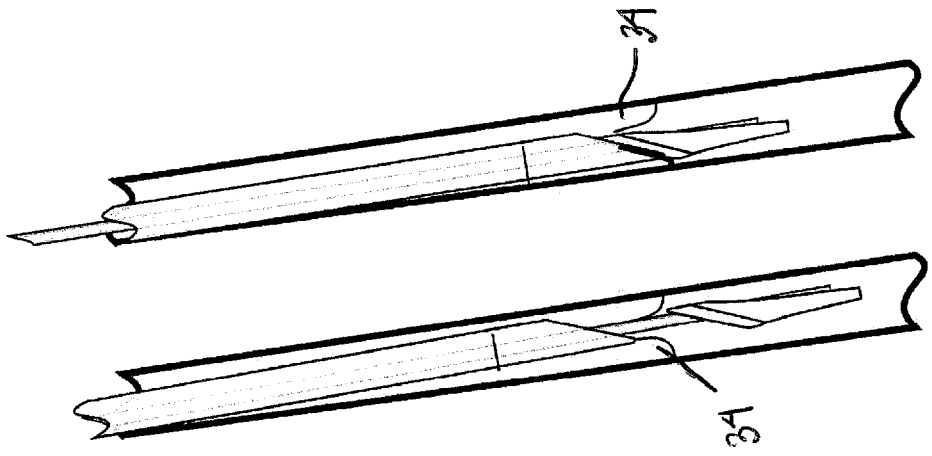

After creation of the Distal Anastomosis the Ellipsys like device can then be used to eliminate valves between the Distal Anastomosis and the Desired Proximal Anastomosis Site. The device can be positioned such that it captures the petals of the valve and then energized to eliminate the valve enabling retrograde flow in the vein.

Figure 8

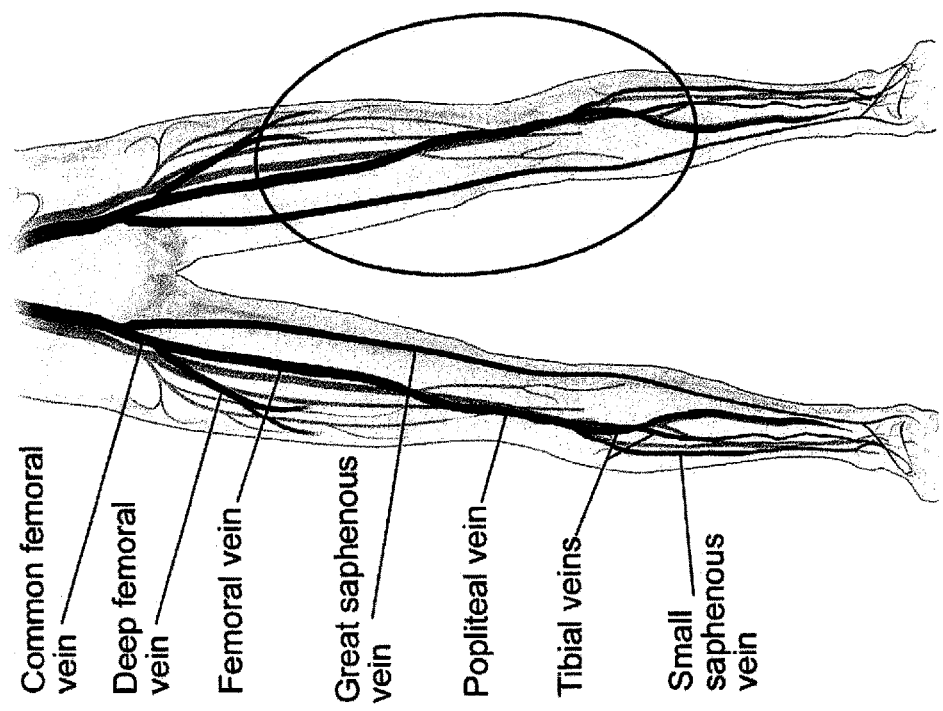
Figure 9: General anatomy of the leg showing veins and arteries.

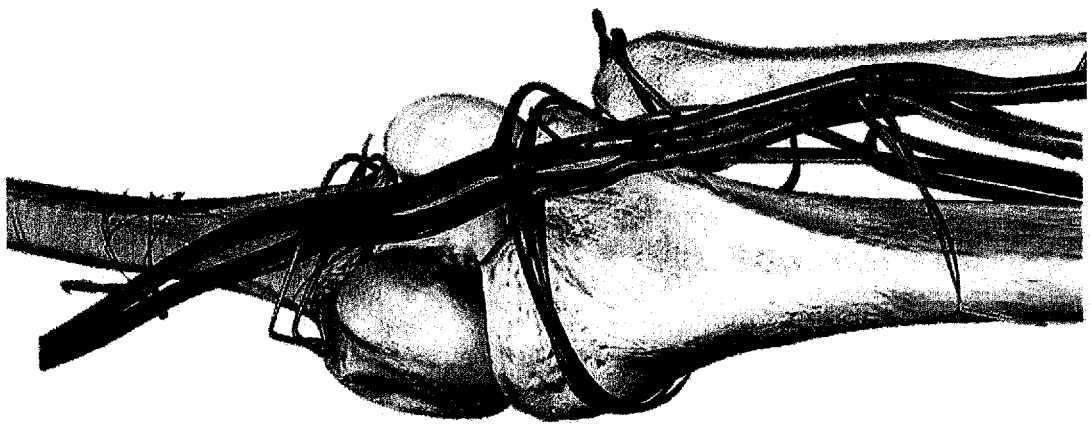
Figure 10: General anatomy of knee area showing the popliteals.

Figure 14: Image showing distal anastomosis and bypass region within which valves are to be eliminated.

Figure 18: Image showing blood flow through bypass.

Figure 19: Side access needle

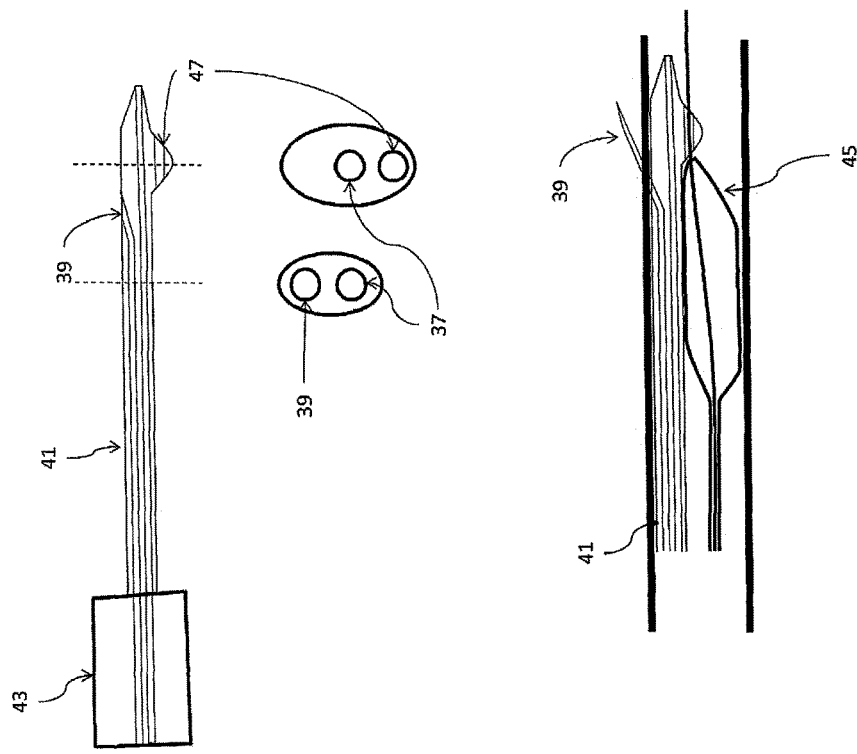
Figure 21: Side access needle

PERCUTANEOUS ANASTOMOTIC DEVICE USED TO CREATE A NATIVE VESSEL BYPASS

This application claims the benefit under 35 U.S.C. 119(e) of the filing date of Provisional U.S. Application Ser. No. 62/948,689, entitled Percutaneous Anastomotic Device Used to Create a Native Vessel Bypass, filed on Dec. 16, 2019, and of the filing date of Provisional U.S. Application Ser. No. 63/039,681, entitled Percutaneous Anastomotic Device Used to Create a Native Vessel Bypass, filed on Jun. 16, 2020. Each of the foregoing applications are expressly incorporated herein by reference, in their entirety.

BACKGROUND OF THE INVENTION

Patients that have occlusions in their arteries experience reduced flow and ischemia to their distal extremities. In many cases, these patients undergo large scale vascular surgeries to bypass the occlusion and restore circulation to the affected extremities or undergo amputations to remove tissues that are not receiving adequate perfusion. Patients that suffer from significant obstruction in the arteries are often classified as suffering from Critical Limb Ischemia (CLI). In patients suffering from CLI, the lack of blood flow in one or more extremities can lead to severe pain and even ulcers or non-healing wounds. Many of these patients are classified as "No Option", meaning that traditional surgical or interventional techniques are unable to restore blood flow through these diseased arterial vessels. This often results in amputation. The inventive percutaneous procedure utilizes native vessels without relocation to create a native vessel bypass to perfuse blood to ischemic extremities in patients with total occlusions of the artery. In some cases, with diffuse disease in the distal artery, the native distal vein may be arterialized to perfuse distal tissues. This approach is faster, less invasive, lower risk, and much less expensive overall than existing vascular surgical techniques.

SUMMARY OF THE INVENTION

The present invention, in one exemplary embodiment, includes a method of creating a native vessel bypass percutaneously, which comprises steps of selecting a target procedural site adjacent to a paired artery and vein, usually near an occlusion or blockage disposed in the artery, inserting a needle into the vein, and then through walls of each of the artery and vein until a distal end of the needle extends into the artery, and placing a guidewire through holes in the paired artery and vein created by the needle. A catheter is advanced over the guidewire so that a distal tip thereof is disposed in the artery, the catheter comprising a proximal base having a distal-facing surface, and the distal tip comprising a proximal-facing surface, the distal tip and proximal base being relatively movable from a first position wherein the proximal-facing surface and the distal-facing surface are in close proximity and a second position wherein the distal tip is spaced distally from the proximal base, the advancing step including moving the proximal base and the distal tip to the second position. The distal tip and the proximal base are moved, relative to one another, by moving the distal tip, the proximal base, and/or both, to the first position, thereby capturing tissue forming vessel walls between the artery and the vein between the proximal-facing surface and the distal-facing surface. Heat is then applied to the captured tissue to ablate the tissue and form an anastomosis between the artery and the vein. The venous valves are disabled to permit retrograde venous flow of arterial blood.

An additional method step is to embolize the vein downstream of the anastomosis to prevent blood flow in the downstream direction, typically by coiling the central vein. The anastomosis is adjacent to one end of the occlusion, and the method may comprise further tracking the needle and guidewire to a position adjacent to the other end of the occlusion. In such case, the method further comprises using the catheter to create a second anastomosis between the vein and the artery, so that one of the anastomosis and the second anastomosis is upstream of the occlusion and the other of the anastomosis and the second anastomosis is downstream of the occlusion with respect to arterial flow.

The needle inserting step may further comprise retracting stabilizing elements disposed on a shaft of the needle while the needle is moving through the vein and then deploying the stabilizing elements once the needle is in place at the target procedural site. A balloon may be inflated adjacent to the needle to seat the needle against the wall of the vein and to push the stabilizing elements around the artery. The heat applying step may comprise using closed loop thermal control to control the tissue ablation and to weld tissue defining the created anastomosis. The heat applying step may also comprise applying a heat gradient across a surface of a heater disposed on one of the proximal-facing and distal-facing surfaces, so that a center portion is hotter to ablate tissue and edge portions are cooler to denature and fuse tissue.

The step of disabling the venous valves may comprise using the catheter to move through the vein and to apply heat to each valve sufficient to ablate the valve. In such a case, each venous valve may be captured between the proximal-facing and distal-facing surfaces and heat is then applied to the captured valve to ablate the valve. The heating profile to ablate each valve is less than 1 second to minimize thermal spread and to minimize any constriction of the vein.

The needle may comprise a side access needle.

The invention, together with additional features and advantages thereof, may best be understood by referencing the following description in conjunction with the accompanying specifications.

BRIEF DESCRIPTION OF THE DRAWINGS

FIG. 8 is a schematic view showing the catheter in use for the purpose of vein valve elimination;

FIG. 9 is a schematic depiction similar to FIG. 1 of the general vasculature of a patient's legs, wherein the general target area of a second exemplary embodiment of a device for creating a native vessel bypass is illustrated;

FIG. 10 is a schematic illustration of the general anatomy of a knee area showing the popliteals;

FIG. 21 is a view further illustrating features of the side access needle.

DETAILED DESCRIPTION OF THE INVENTION

Notation and Nomenclature

Figure 1:
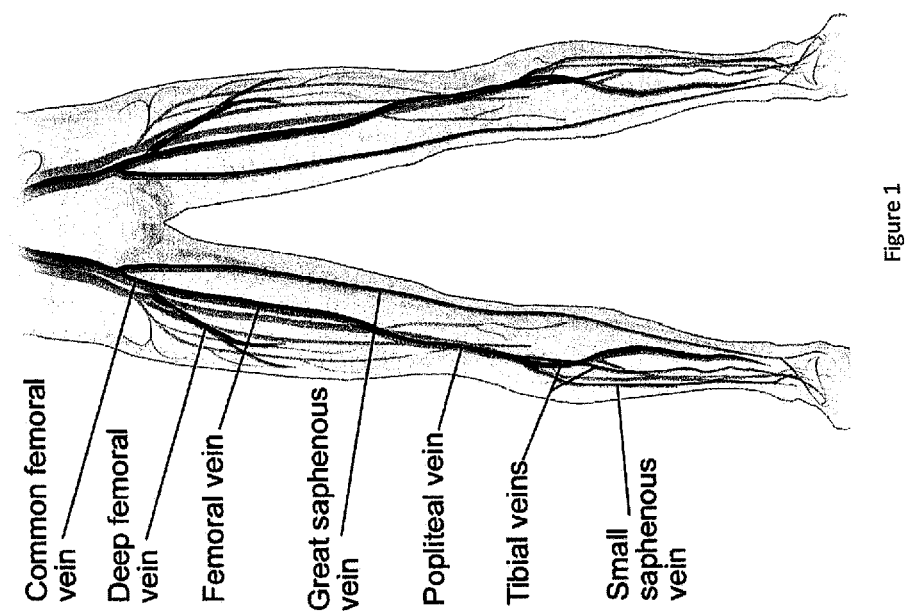
FIG. 1 is a schematic depiction of the general vasculature of a patient's legs.

Certain terms are used throughout the following description and claims to refer to particular system components. As one skilled in the art will appreciate, companies that design and manufacture medical devices may refer to a component by different names. This document does not intend to distinguish between components that differ in name but not function.

In the following discussion and in the claims, the terms "including" and "comprising" are used in an open-ended fashion, and thus should be interpreted to mean "including, but not limited to"

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent application and hardware) is expressly incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Referring now more particularly to the drawings, there are shown and described herein representative procedures and two related representative devices for performing those procedures. One of the devices comprises a catheter constructed similarly to the catheter manufactured and marketed by the Applicant, Avenu Medical, Inc. of San Juan Capistrano, California, under the registered trademark ELLIPSYS. The other illustrated device is a needle for obtaining guidewire access between vessels. The procedure and devices shown and described herein may be used for the creation of anastomoses and the elimination of valves in the venous structure to create a native vessel bypass.

As illustrated in FIG. 1, the vessels of the leg may exhibit favorable anatomy for using an adjacent vein to bypass an occlusion of the artery. Although the leg may be the most common application for this technology any location within the body where a vein and artery are within close proximity can be used. Appropriate paired vessels may include the femoral artery and vein, the popliteal artery and vein, the tibial artery and vein, the brachial artery and vein, the radial artery and vein, the ulnar artery and vein, and any other tubular structure in the body where two lumens come into close proximity (typically less than 2 mm).

Figure 2:
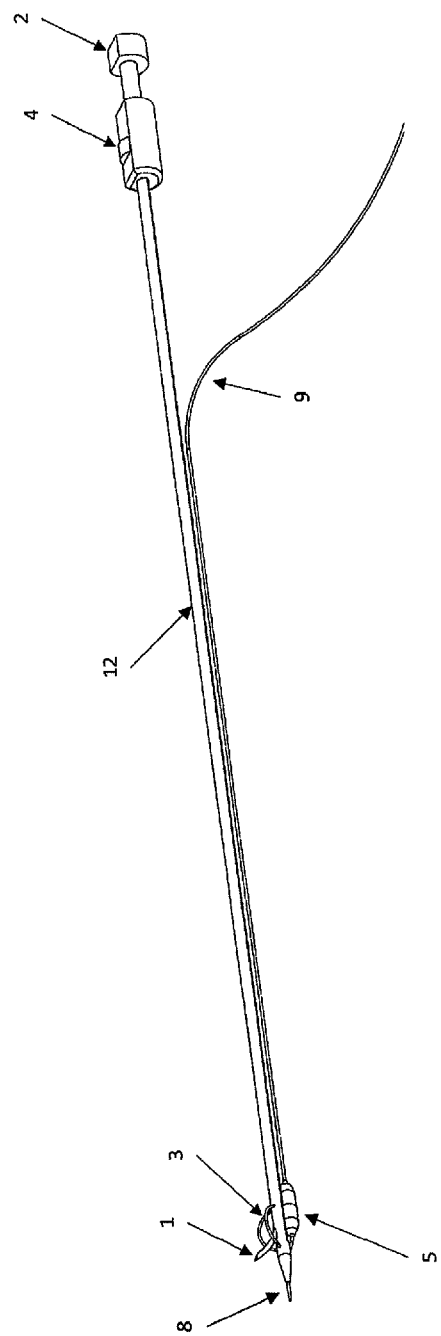
FIG. 2 is an isometric view of an exemplary embodiment of a needle device constructed in accordance with the principles of the present invention.
Figure 3:
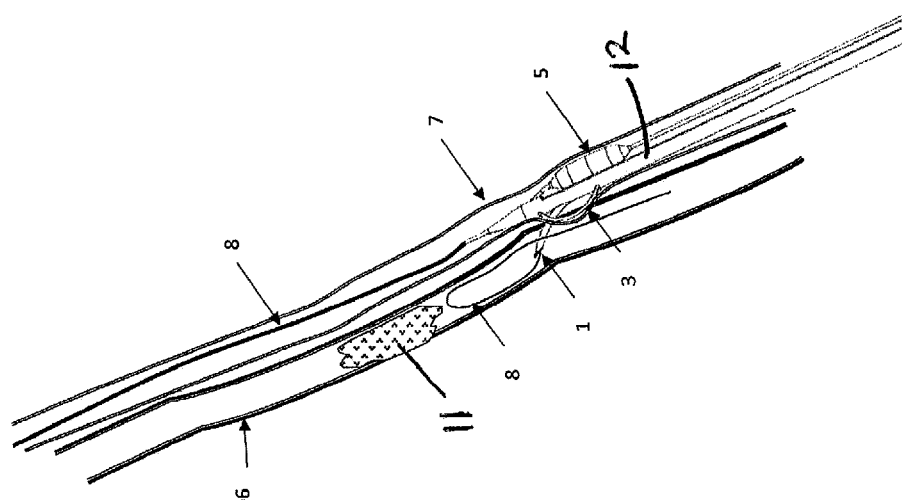
FIG. 3 is an illustration of an occlusion and favorable anatomy with a paired artery and vein.

In FIG. 2, there is illustrated a representative embodiment of a needle device usable in connection with the inventive methods. The needle device comprises a retractable curved needle 1, a needle advancement hub 2, a stabilizing element 3, a stabilizing element actuator 4, a semi-compliant angioplasty balloon 5, a guidewire 8, an angioplasty balloon catheter shaft 9, and a needle shaft 12. FIG. 3 illustrates a target procedural site in one of the patient's legs, wherein there are an artery 6 and vein 7 adjacent to one another. As illustrated, the site was selected because of an arterial blockage or occlusion 11 in the artery 6.

In a representative procedure, the distal vein 7 is punctured first, the vein being more superficial. It is easier to track over the guidewire 8 through the valves antegrade. If the vein is too small, a proximal puncture may be used. A feature, such as a flat, an ink marking, or a boss on the needle hub 2 to indicate the direction the needle will protrude from the needle shaft 12. The needle shaft 12 is flexible, but has features such as a braided or laser cut shaft to provide good torque response and rotational accuracy. Stabilizing elements 3 are retracted during device insertion and then deployed once the needle is in place.

The tip of the needle has a short guidewire lumen which is concentric with the tapered tip, but the lumen exits the catheter opposite of the needle. The balloon 5 can track over the guidewire until it reaches the guidewire lumen of the needle. The balloon can be inflated under the needle to seat it against the wall. This supports support for the needle as it advances and also causes the stabilization element to engage around the artery.

In FIG. 3 the balloon is inflated under the side access needle with the needle and guidewire in the artery 6. The orientation of the artery and vein are determined by using ultrasound. Rotation of the needle is controlled by the needle hub to match orientation determined by ultrasound or radiopaque markers under fluoroscopy. The stabilizing element 3 on the needle is deployed to engage around the artery to center the needle on the artery. These features also ensure that the needle does not skive off of the artery during needle extension.

The balloon 5 pushes the stabilizing features 3 around the artery 6. The vein 7 is thin-walled, so it allows the venous wall to conform around the artery. The needle can be used with or without the balloon. Different-sized balloons can be used, depending upon how big the vessel is (ranges from 2-8 mm).

The stabilizing elements 3 are retractable, so that the needle is low profile going through the sheath. They can be made from shape memory alloy, such as Nitinol, or wire that buckles into a curve. The elements 3 can be retracted using a rotational advancement actuator on the hub 2.

Figure 4:
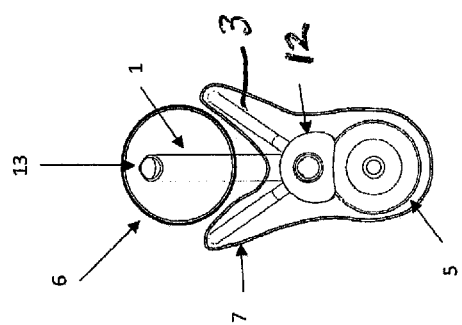
FIG. 4 is a cross-sectional view of a balloon needle and stabilization wires of the invention.

Now with reference to FIG. 4, which is a cross-section of the balloon needle and stabilization wires, it can be seen that the stabilizing element 3 engages the artery and the balloon pushes the needle against the artery. The vein wall is thin and compliant, which allows the venous wall to wrap around the artery, essentially locking the needle in place. This ensures that the puncture is centered on the artery. Different balloon sizes can be used depending on the size of the vein and how much interference is needed between the stabilizing elements and the artery. Typical balloon sizes range from 2-10 mm.

Figure 5B:
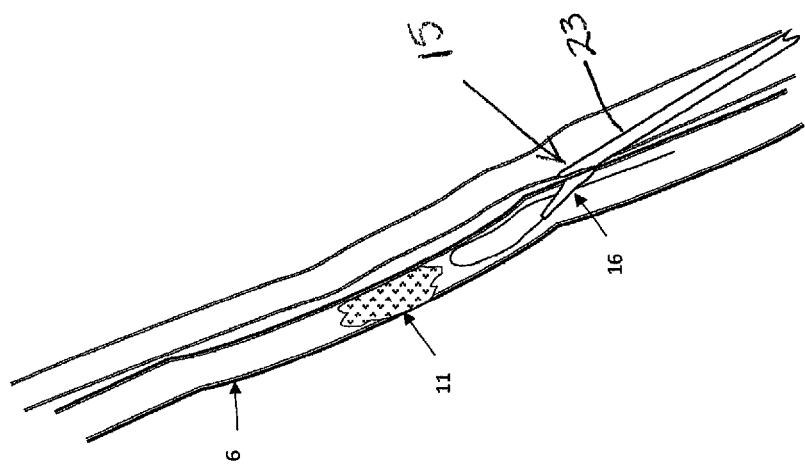
FIG. 5b is a view similar to FIG. 5a showing the catheter capturing portions of the artery and vein.
Figure 5A:
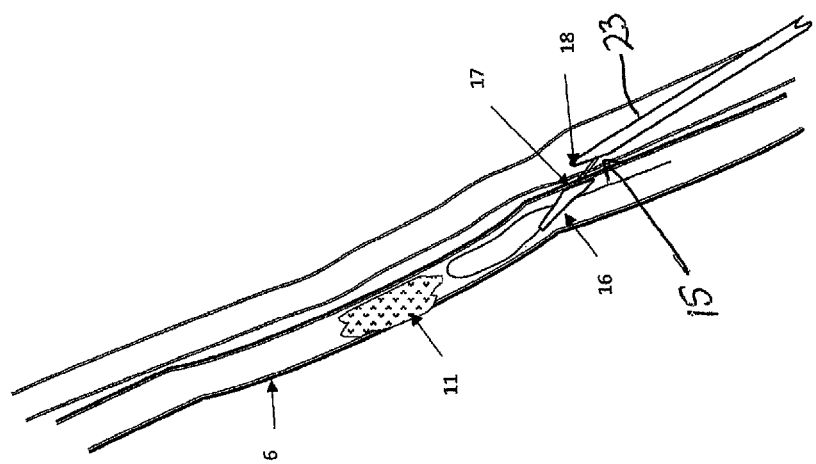
FIG. 5a is a view illustrating an exemplary catheter constructed according to the principles of the present invention inserted into the artery.
Figure 6:
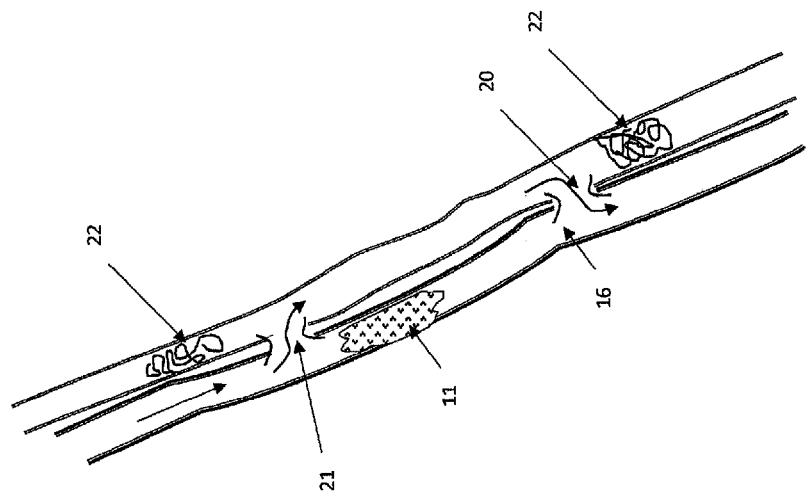
FIG. 6 is a view similar to FIGS. 5a-5c wherein both anastomoses have been formed to bypass the occlusion and the central vein coiled to prevent antegrade flow up the vein.

In FIG. 5a a catheter 15 has been inserted into the artery, over the guidewire, to form and create a distal anastomosis 20 (FIG. 6). The catheter may be of the type disclosed in commonly assigned U.S. Pat. Nos. 9,439,710, 9,452,015, and 9,474,562, for example, herein expressly incorporated by reference, in their entirety, and currently sold under the trademark ELLIPSYS® by the assignee, Avenu Medical, Inc. of San Juan Capistrano, CA. A distal tip 16 is tapered like a dilator in order to track over the guidewire and to penetrate through the vessel walls. A barb is provided on the proximal end of the distal tip to engage the arterial wall. An angled proximal-facing surface 17 is provided on the distal tip 16, which corresponds with an angled distal-facing surface 18 on a proximal base 23 to cut longer anastomoses than the diameter of the catheter 15.

FIG. 5b illustrates the catheter capturing the artery and vein. An opposite barb is disposed on the venous side to catch the vein wall. Pressure is applied between the artery and vein. Heat is applied to ablate tissue captured in the center of the catheter, and the outer edge of the tissue is sealed by tissue fusion. Clips may be applied to stabilize the anastomosis, if desired. Depending on the desired blood flow rate, the anastomosis may be balloon dilated immediately after the artery and vein are fused together to increase the volume of blood through the anastomosis.

Figure 5C:
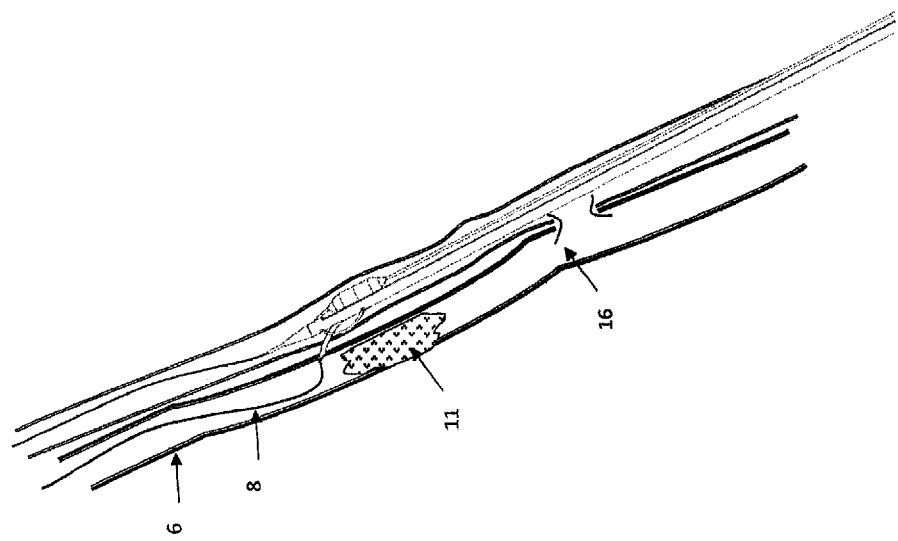
FIG. 5c is a view similar to FIGS. 5a and 5b illustrating the completion of a distal anastomosis and the needle tracked up to a desired location for a proximal anastomosis.

In FIG. 5c, the distal anastomosis is complete, and the needle is tracked up to a desired location to create a proximal anastomosis 21. Different variations of which anastomosis is created first are possible. In one approach, the needle may be used to place one wire distal to the blockage and then re-position the needle and place another wire prior to creating the anastomosis. In some cases, where there is no viable artery distal to the occlusion, only a single anastomosis is created, and the central vein is embolized and the venous valves are stripped to allow retrograde venous flow. The pressurized retrograde venous flow perfuses the tissue through the un-diseased venous bed.

FIG. 6 illustrates an overview of the anatomy at the procedural site, with two anastomoses 20, 21 created to bypass the blockage, and a central vein coiled (insertion of coils 22 to block flow through the vein 7) to prevent antegrade flow up the vein. Valves are stripped in the vein to pressurize the venous system to force flow into the distal artery. Side branches in the vein are also embolized to prevent flow into collateral veins. The veins may be embolized at the time of procedure or at a later date. It may be beneficial to create the distal anastomosis to let the vein grow and mature from fistula flow. After a few weeks, the patient is brought back to create the proximal anastomosis and embolize central veins. This may be beneficial in patients with small anatomy or patients with an increased risk of the anastomosis thrombosing. Alternatively, both anastomoses are created at index procedure and let mature. After a few weeks, the central and distal veins are embolized. And finally, in patients with sufficient flow through the anastomosis, the central veins are embolized at the time of procedure to force the flow into the distal artery.

Figure 7:
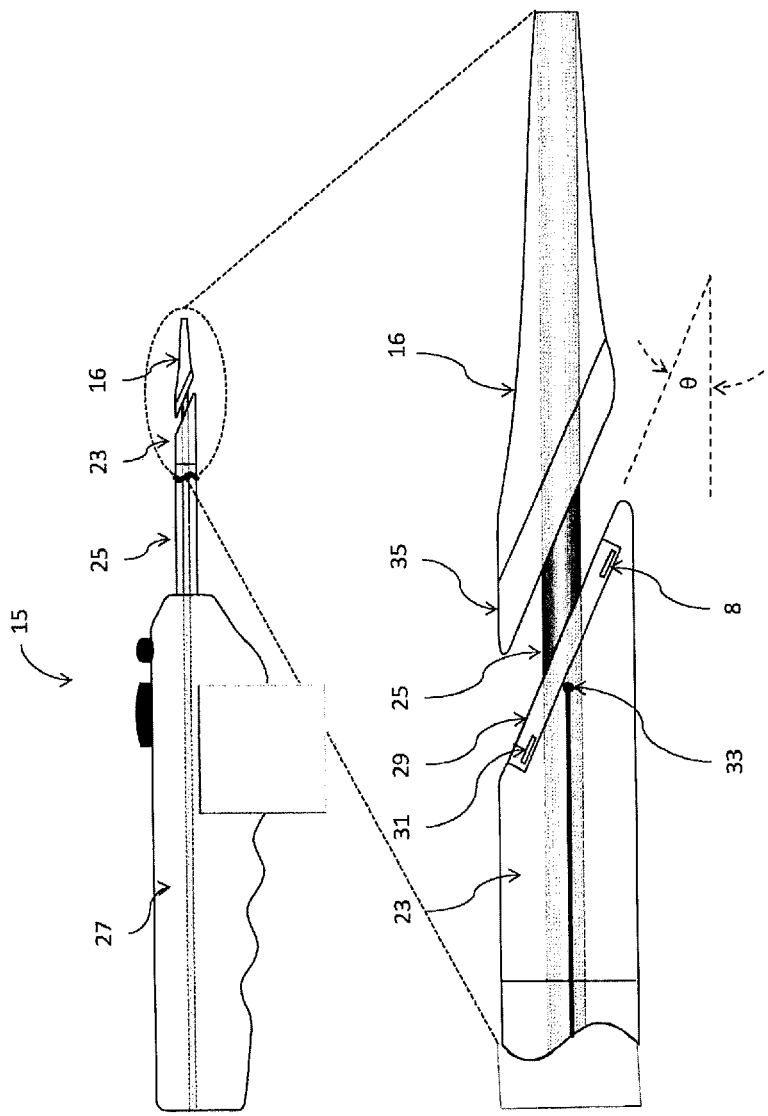
FIG. 7 is an illustration of the catheter shown schematically in FIGS. 5a-5b, including an inset comprising an enlarged illustration of the distal end of the catheter.

FIG. 7 shows a catheter device 15 as described above, suitable for use in performing the inventive methods. Closed loop thermal control is utilized to control tissue ablation and welding, and there is a gradient across the surface of the heater 29, with the center portion hotter to ablate tissue and cooler around the outer edge to denature and fuse tissue. There is a recess in the center portion to capture tissue. A position sensor ensures proper positioning and automatically stops applying heat when the heating element closes. The catheter device comprises, in addition to those elements already discussed above, a proximal base 23, a catheter shaft 25, which may be flexible, a handle 27 for manipulating and actuating the catheter 15, and a heater element 31, which is illustrated as being disposed on the distal-facing surface 18 of the proximal base 23, but may alternatively be disposed on the proximal-facing surface 17 of the distal tip 16, or, optionally, heating elements may be disposed on both surfaces 17, 18. A heat spreader 29 is disposed on the surface 18, and a distal heat spreader 35 is disposed on the surface 17. A thermocouple 33 is disposed on the proximal base, as shown. The catheter has a guidewire lumen.

In FIG. 8, the catheter described above is used to engage and make the vein valves 34 incompetent. The catheter is either advanced or retracted to engage the valve 34. The catheter may be advanced over a guidewire to help it navigate through the valves. The tip is closed to capture the valve between the heating elements, and then heat is applied to ablate the valve. The heating profile is short (<1 second) to minimize thermal spread and to prevent any constriction of the vein.

Figure 11:
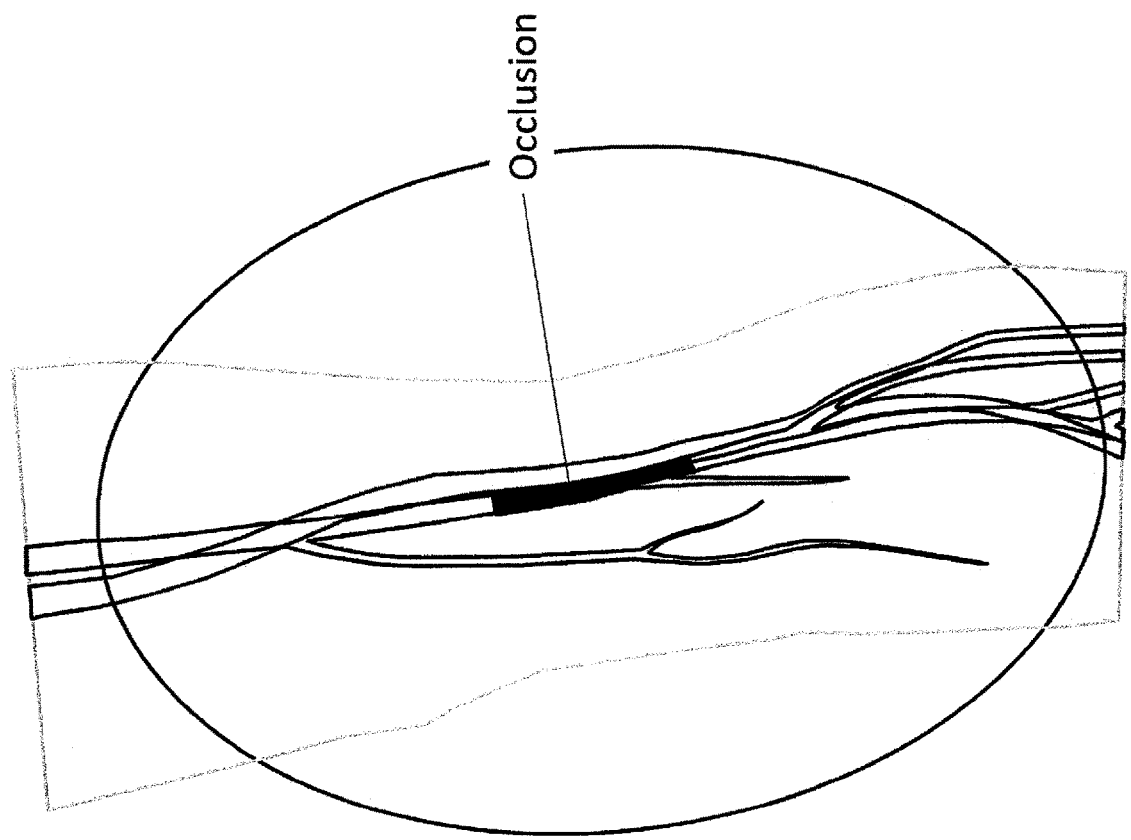
FIG. 11 is a schematic view showing an artery with an occlusion in the target area.

A second exemplary embodiment is illustrated in FIGS. 9-21. FIG. 9 is similar to FIG. 1, as discussed in connection with the needle embodiment already described and shown in FIGS. 1-8. FIG. 10 illustrates the vessel anatomy behind the knee where occlusions may occur and also the position of a paired artery and vein selected as a target site in a particular method according to the invention. FIG. 11 shows the location of an occlusion in an artery and favorable anatomy with a paired artery and vein in the target site in a patient's knee. The intended region for the bypass includes the target native vessels and the occluded vessel lumen. The intended anastomosis sites must be located appropriately to achieve the desired bypass solution and should meet the criteria for vessel proximity. Venous access is preferred for the procedure, in order to reduce risk associated with arterial access. Accessing the vein can be done proximally of or distally to the bypass region. There may be advantages to accessing in the direction of venous blood flow (distal access for navigating past the valves 34. The target sites for anastomosis should not exceed 2 mm of separation in preferred approaches.

Figure 12:
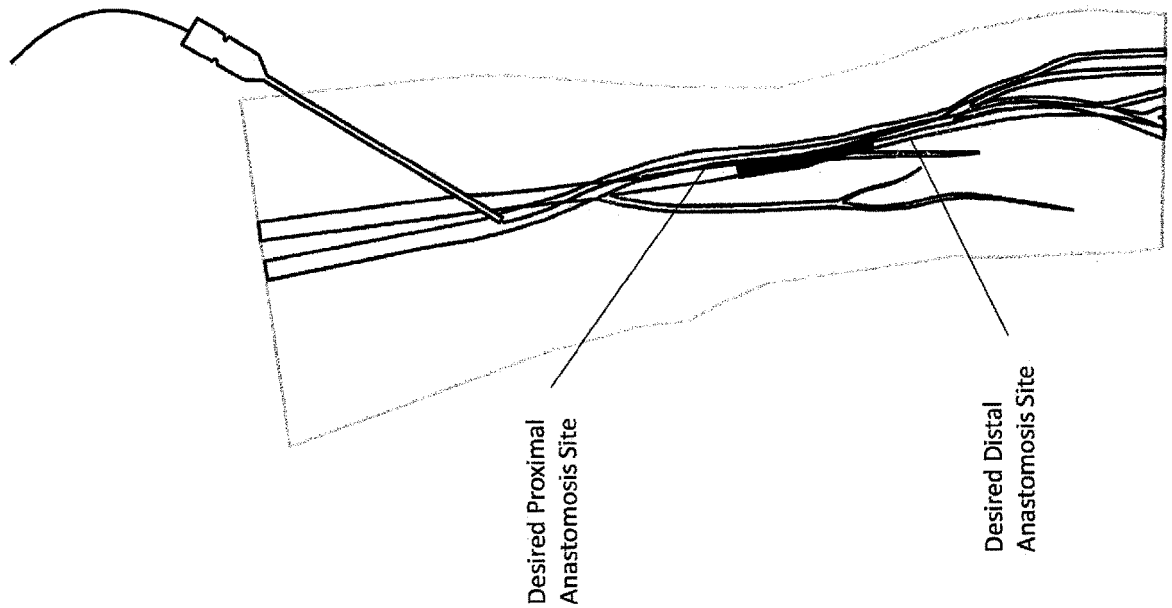
FIG. 12 is a schematic illustration showing venous access, guidewire placement and target sites for an anastomosis in accordance with the second exemplary embodiment.

FIG. 12 shows the desired target proximal and distal anastomosis sites that allow blood to bypass the occluded artery, as well as desired venous access and guidewire placement sites. Venous access may be gained proximally or distally of the occlusion, there may be advantages or disadvantages of accessing from one side or the other. Distal access may provide easier passage of any valves in the vein. Accessing from both distal and proximal directions might be advantageous for proximity to a desired anastomosis site and improve device feedback while attempting to aim/steer the needle utilized for crossing into the artery. Whether via ipsilateral or contralateral approach, venous access is gained proximal to the desired anastomosis sites in one exemplary approach. A sheath/guide catheter is placed as a conduit for percutaneous devices to be utilized, such as guidewire, guide catheter, catheter, etc. Guidewire access may then be obtained sufficiently distal to the distal anastomosis site.

Figure 13:
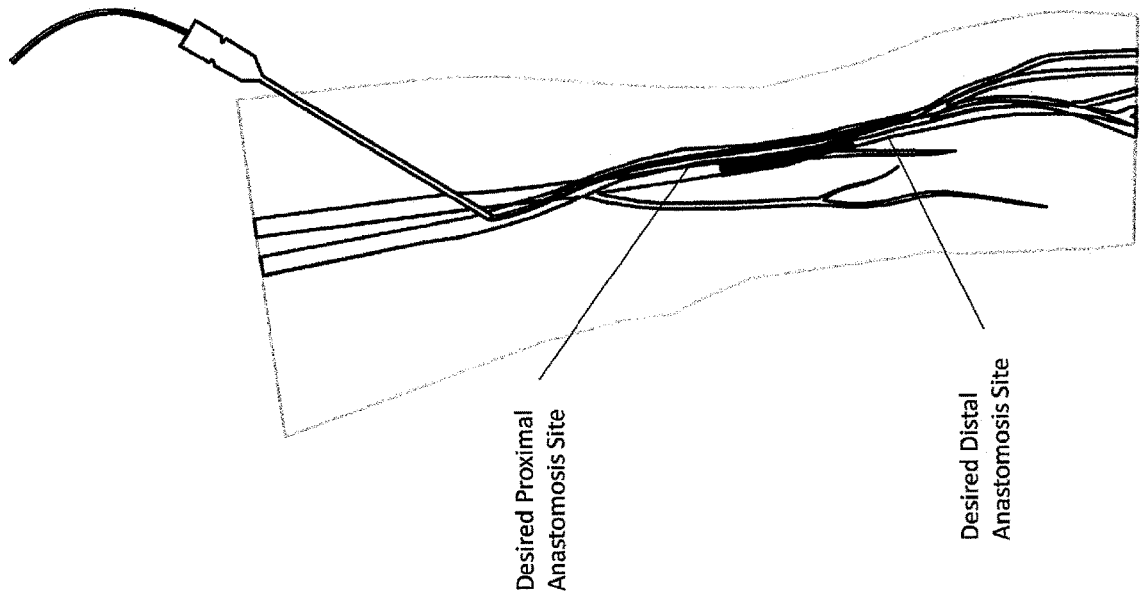
FIG. 13 is an illustration showing side access needle placement.

FIG. 13 illustrates side access needle placement. Utilizing a side access needle to puncture into the artery may present challenges for the physician to visualize the needle and aim it properly at the artery. Using ultrasound or other suitable imaging systems for visualization allows the operator to see both vessels and the device in real time. There are several ways of improving echogenicity of devices which may include facets, coils, etc. and may be employed in the design of the device to aid in visualization and aiming. Additional features such as vibration of individual elements (e.g. needle and/or guidewire) make the device easier to identify under ultrasound visualization. Imparting a small amplitude vibration with fixed or variable amplitudes to the proximal end of the device/element with fixed or variable frequencies improves visibility and aiming. An angioplasty balloon can also be inserted and placed next to the crossing needle in the vein and then inflated to provide stabilization during crossing. It is possible that an array of balloons deployed could provide the best stability for the crossing needle. In this case a feature(s) on the shaft of the crossing needle may facilitate the positioning of the balloons in an optimal way by orienting and holding the guidewire of the balloon used to stabilize the needle.

Continuing with a description of an exemplary method, a needle designed to puncture from the vein into the artery at the desired distal anastomosis site is then tracked over the guidewire. This needle may be a multilumen catheter comprised of a lumen for tracking over a guidewire and a lumen for a second guidewire, to be placed into the artery after the needle punctures the artery. After this step, there should be two guidewires, a first guidewire that remains in the vein distal to the distal anastomosis site, and a second guidewire that starts in the vein and crosses into the artery at the distal anastomosis site.

Figure 14:
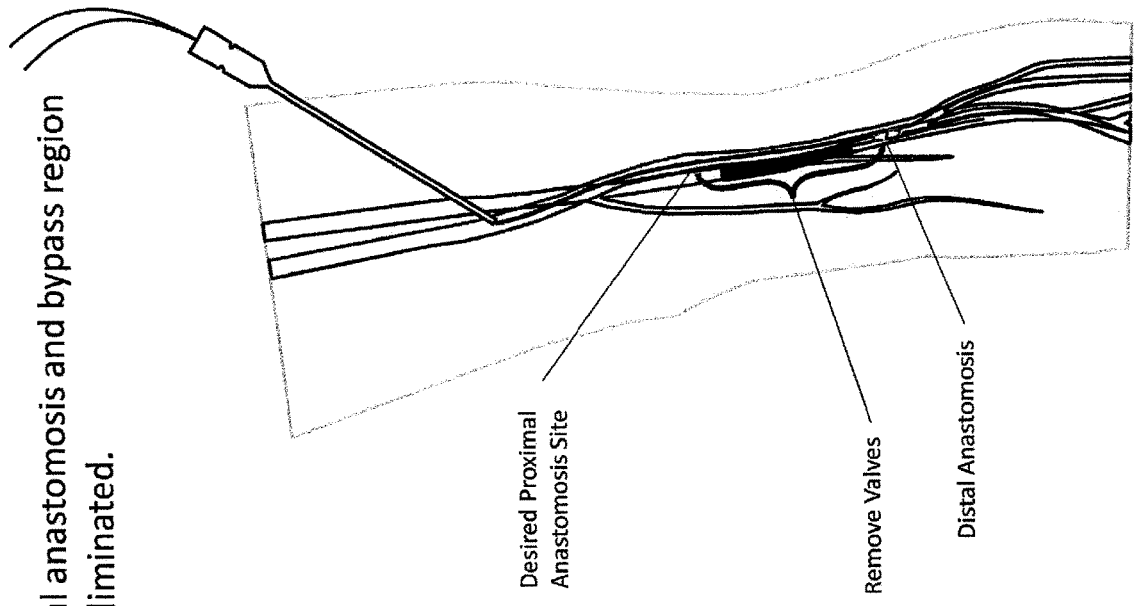
FIG. 14 is an illustration showing a distal anastomosis and bypass region within which valves are to be eliminated.

FIG. 14 shows the distal anastomosis after creation. Once arterial access is obtained, a guidewire is placed and then a catheter of the type discussed above and shown in FIG. 7, which is similar to the catheter systems sold by the assignee under the trademark ELLIPSYS®, may be used to create the anastomosis.

Figure 15:
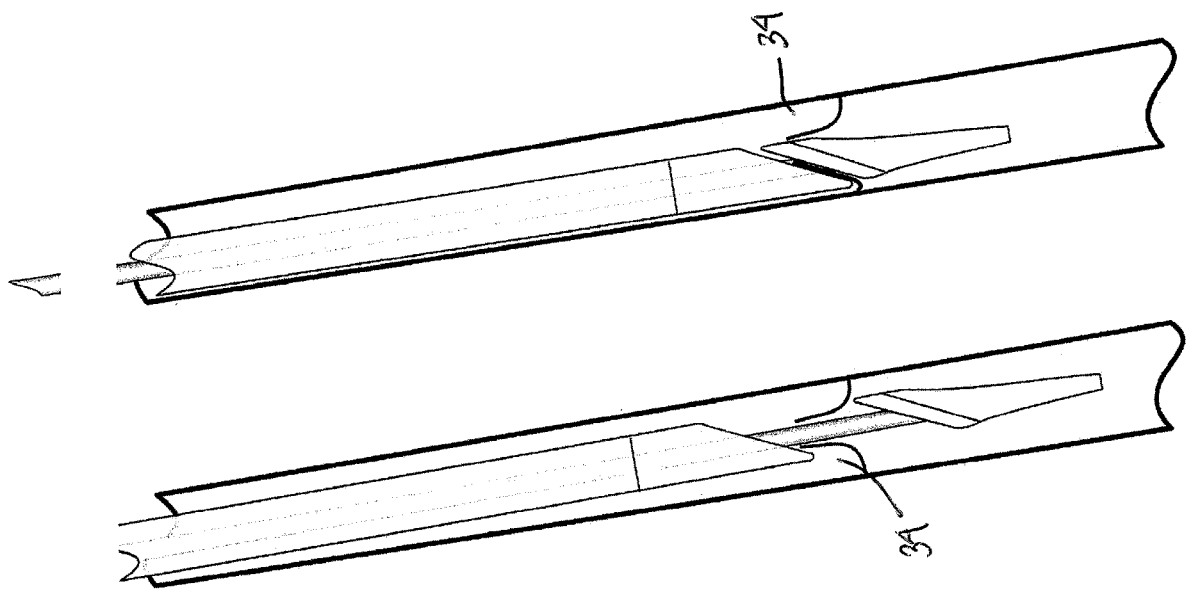
FIG. 15 is an illustration showing valve elimination using a device constructed in accordance with the principles of the invention.

FIG. 15 illustrates the use of the aforementioned catheter for elimination of valves 34 within the bypass region of the vein. More particularly, after creation of the distal anastomosis, as discussed above in connection with FIG. 14, the catheter may then be used to eliminate valves between the distal anastomosis and the desired proximal anastomosis site. The device is positioned so that it captures the petals of each valve 34 between its corresponding surfaces 17, 18, and is then energized to eliminate the valve, thereby enabling retrograde flow in the vein.

Figure 16:
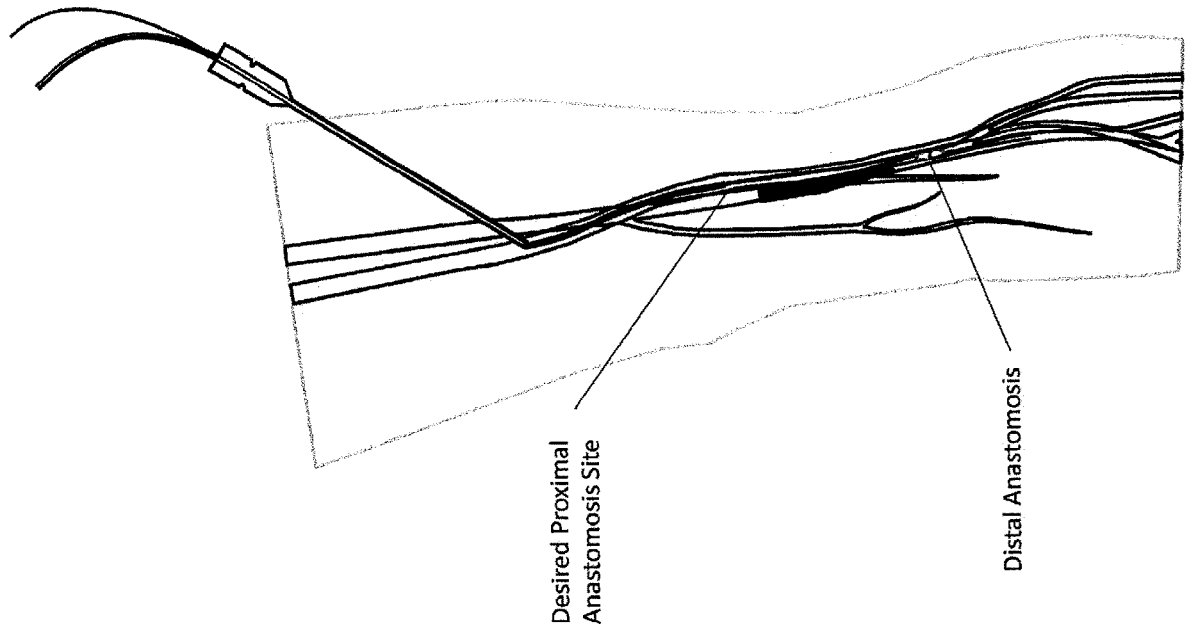
FIG. 16 is an illustration showing a proximal anastomosis crossing.
Figure 17:
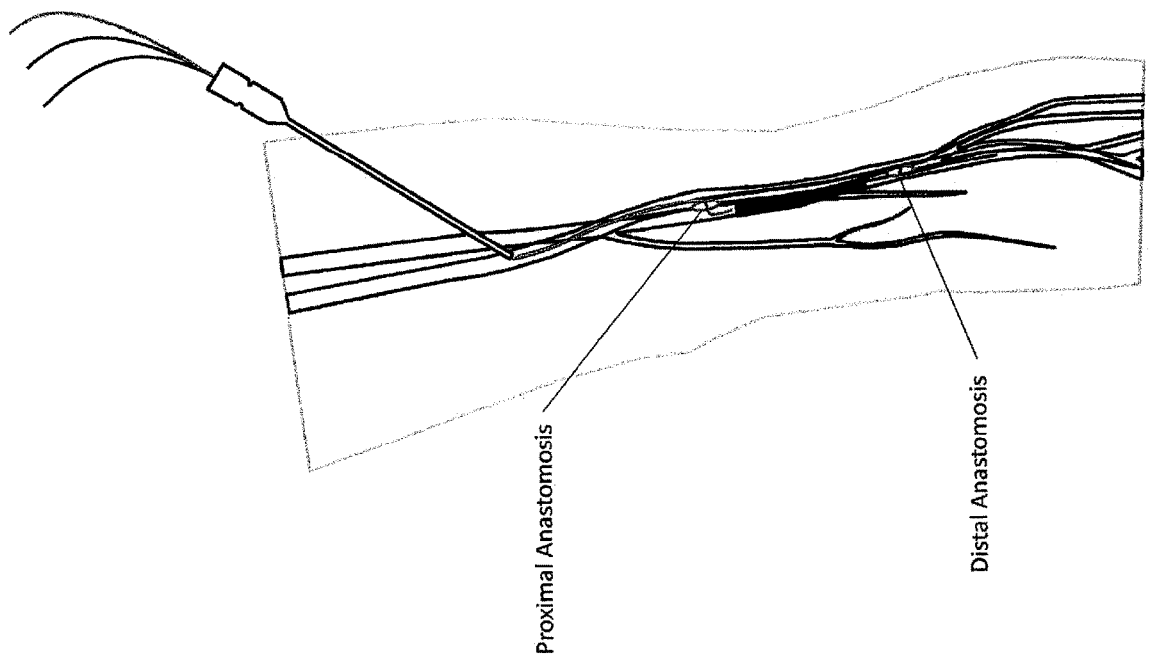
FIG. 17 is an illustration similar to FIG. 16 showing a proximal anastomosis creation.

FIGS. 16 and 17 illustrate the creation of a second proximal anastomosis to complete the bypass. Ligation or embolization of the proximal vein may be performed during the procedure or later to direct flow to the distal extremity. FIG. 16 shows the proximal anastomosis crossing. The needle used previously to puncture from the vein into the artery for the distal anastomosis is utilized again to puncture from the vein into the artery at the at the desired proximal anastomosis site. A third guidewire is then placed into the artery proximal to the occlusion.

FIG. 17 shows the proximal anastomosis creation. The catheter is deployed over the third guidewire and used to create the proximal anastomosis, in a manner similar to that discussed above with respect to creation of the distal anastomosis.

If all three guidewires are kept in their designated locations, balloon catheters may be utilized to dilate either anastomosis or the vein to ensure that flow around the occlusion is established. Coil embolization may be utilized in the vein proximal to the proximal anastomosis to direct flow distally in the vein.

Figure 18:
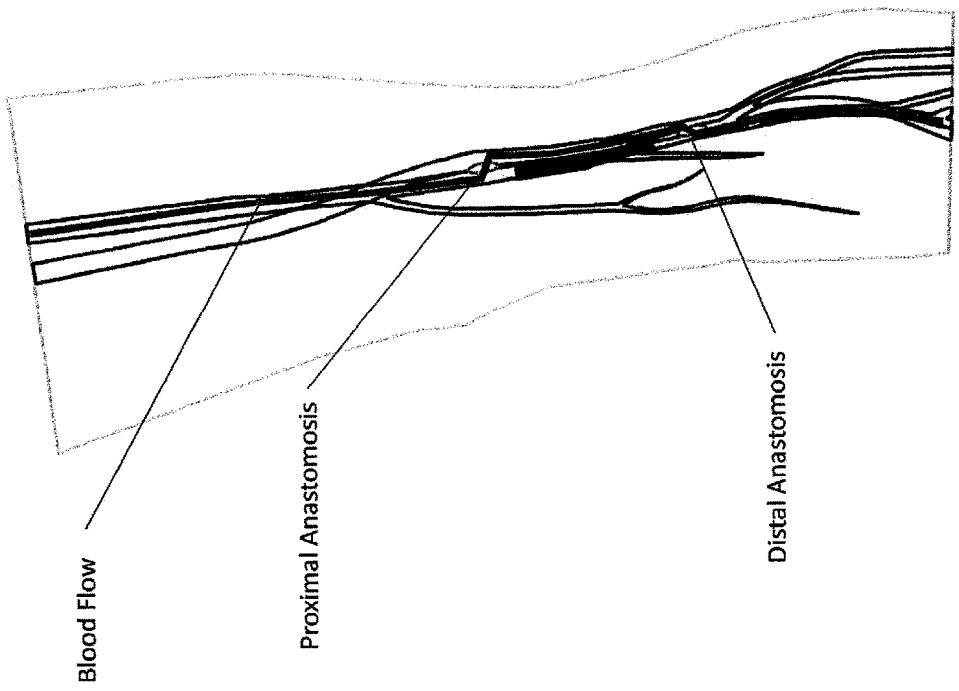
FIG. 18 is an illustration showing blood flow through the bypass once it has been created.

FIG. 18 shows the flow of blood around the occluded artery through the newly created native vessel bypass. The blood will now flow from the proximal anastomosis to the distal anastomosis, bypassing the occlusion in the artery and perfusing the distal anatomy.

Depending on the location of the occlusion, an alternate procedure may be used to create only a proximal anastomosis. Elimination of the distal valves in the vein may then utilize the entire distal vein to perfuse the affected extremity.

Figure 19:
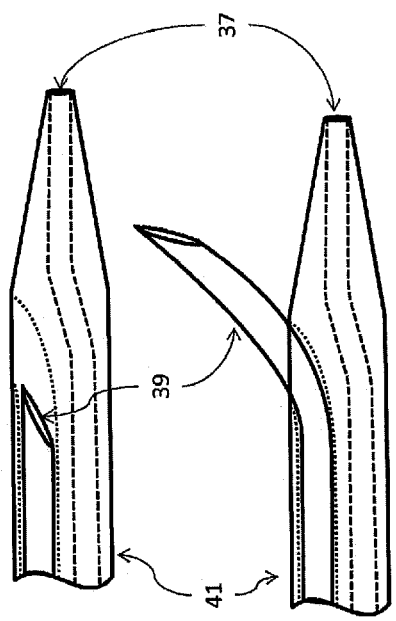
FIG. 19 is a plan view showing the device of FIG. 15 in greater constructional detail.
Figure 20:
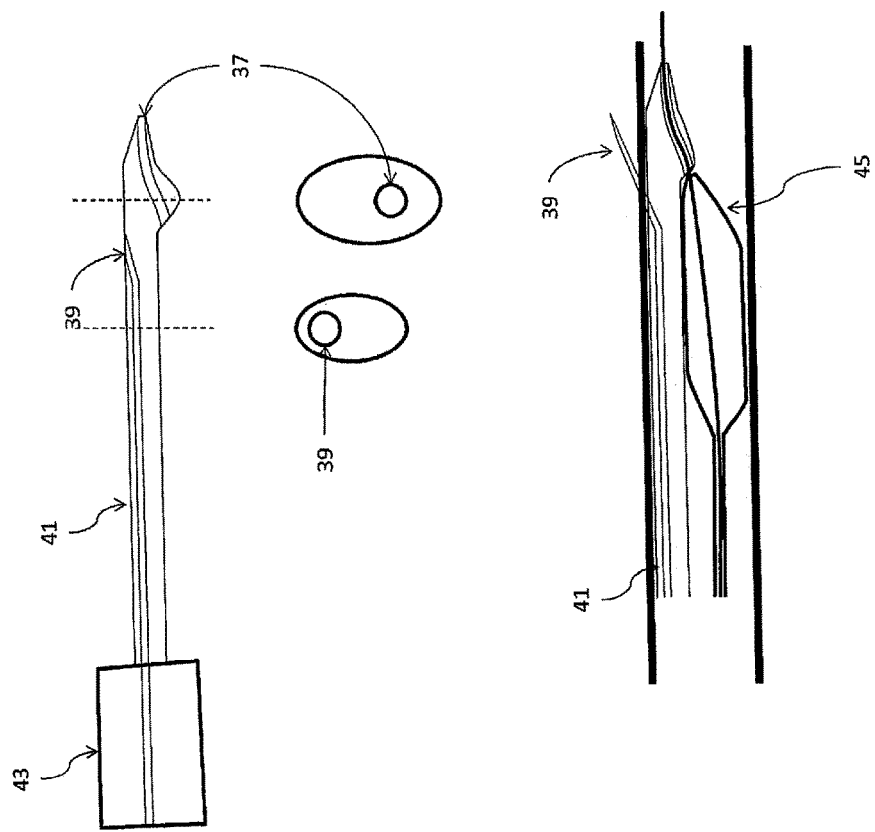
FIG. 20 is a view showing an extensible side access needle which may be used in connection with the inventive approach.

FIGS. 19-21 illustrates embodiments of the extendable side access needle described above and its features. As shown in FIG. 19, in one exemplary embodiment, these features include a guidewire lumen 37, an extendable needle 39 with a second guidewire lumen, and a shaft 41.

FIG. 20 shows another exemplary embodiment (the two lumen needle) of the extendable lumen needle 39 with the guidewire lumen 37 and second guidewire lumen, and the shaft 41, which may be flexible, but must have torsional stiffness. The device further includes a crossing needle hub 43, which may include an automatic needle advance and/or a vibration inducing element. An angioplasty balloon 45 is inflated for stabilization.

FIG. 21 shows yet another exemplary embodiment (the three lumen needle) of the extendable lumen needle 39 with the guidewire lumen 37 and second guidewire lumen, shaft 41, which may be flexible, but must have torsional stiffness, a crossing needle device hub 43, which may include automatic needle advance and/or vibration inducing element, and an angioplasty balloon 45 inflated for stabilization. An angioplasty balloon guidewire locator 47 is also provided.

Accordingly, although an exemplary embodiment and method according to the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A method of creating a native vessel bypass percutaneously, comprising:
   selecting a target procedural site adjacent to a paired artery and vein;
   inserting a needle into the vein, and then through walls of each of the artery and vein until a distal end of the needle extends into the artery;
   placing a guidewire through holes in the paired artery and vein created by the needle;
   advancing a catheter over the guidewire so that a distal tip thereof is disposed in the artery, the catheter comprising a proximal base having a distal-facing surface, and the distal tip comprising a proximal-facing surface, the distal tip and proximal base being relatively movable from a first position wherein the proximal-facing surface and the distal-facing surface are in close proximity and a second position wherein the distal tip is spaced distally from the proximal base, the advancing step including moving the proximal base and the distal tip to the second position;
   moving the distal tip and the proximal base, relative to one another, to the first position, thereby capturing tissue forming vessel walls between the artery and the vein between the proximal-facing surface and the distal-facing surface;
   applying heat to the captured tissue with the catheter to ablate the tissue and form an anastomosis between the artery and the vein;
   moving the catheter proximally in the vein to position the catheter adjacent venous valves after forming the anastomosis; and
   disabling venous valves to permit retrograde venous flow of arterial blood using the catheter to move through the vein and to apply heat to each valve sufficient to ablate the valves after moving the catheter proximally in the vein to position the catheter adjacent the venous valve.

2. The method as recited in claim 1, wherein the target procedural site is near a blockage or occlusion disposed in the artery.

3. The method as recited in claim 2, wherein the anastomosis is adjacent to one end of the occlusion, the method comprising further tracking the needle and guidewire to a position adjacent to the other end of the occlusion.

4. The method as recited in claim 3, and further comprising using the catheter to create a second anastomosis between the vein and the artery, so that one of the anastomosis and the second anastomosis is upstream of the occlusion and the other of the anastomosis and the second anastomosis is downstream of the occlusion with respect to arterial flow.

5. The method as recited in claim 1, further comprising embolizing the vein downstream of the anastomosis to prevent blood flow in the vein in an arterial flow direction after passing the anastomosis, wherein the embolizing step comprises coiling the central vein.

6. The method as recited in claim 1, wherein the needle inserting step further comprises retracting stabilizing elements disposed on a shaft of the needle while the needle is moving through the vein and then deploying the stabilizing elements once the needle is in place at the target procedural site.

7. The method as recited in claim 6, and further comprising inflating a balloon adjacent to the needle to seat the needle against the wall of the vein and to push the stabilizing elements around the artery.

8. The method as recited in claim 1, and further comprising using closed loop thermal control to perform the heat applying step to control the tissue ablation and to weld tissue defining the created anastomosis.

9. The method as recited in claim 8, wherein the heat applying step comprises applying a heat gradient across a surface of a heater disposed on one of the proximal-facing and distal-facing surfaces, so that a center portion is hotter to ablate tissue and edge portions are cooler to denature and fuse tissue.

10. The method as recited in claim 1, wherein each venous valve is captured between the proximal-facing and distal-facing surfaces and heat is then applied to the captured valve to ablate the valve.

11. The method as recited in claim 10, wherein the heating profile to ablate each valve is less than 1 second to minimize thermal spread and to minimize any constriction of the vein.

12. The method as recited in claim 1, wherein the needle comprises a side access needle.

13. The method as recited in claim 1, further comprising:
   moving the catheter proximally in the vein after disabling the venous valves and advancing the catheter so that the distal tip thereof is disposed in the artery;
   moving the distal tip and the proximal base, relative to one another, to the first position, thereby capturing proximal tissue forming vessel walls between the artery and the vein between the proximal-facing surface and the distal-facing surface; and
   applying heat to the captured proximal tissue with the catheter to ablate the tissue and form a second anastomosis between the artery and the vein.

14. A method of creating a native vessel bypass percutaneously, comprising:
   selecting a target procedural site adjacent to a paired artery and vein;
   inserting a needle into the vein, and then through walls of each of the artery and vein until a distal end of the needle extends into the artery;
   retracting a non-inflatable stabilizing element disposed on a shaft of the needle while the needle is moving through the vein and then deploying the stabilizing element once the needle is in place at the target procedural site;
   deforming the vein with the stabilizing element and extending the stabilizing element on opposite sides of the artery such that the stabilizing element and vein partially surround the artery to center the needle on the artery;

placing a guidewire through holes in the paired artery and vein created by the needle;

advancing a catheter over the guidewire so that a distal tip thereof is disposed in the artery, the catheter comprising a proximal base having a distal-facing surface, and the distal tip comprising a proximal-facing surface, the distal tip and proximal base being relatively movable from a first position wherein the proximal-facing surface and the distal-facing surface are in close proximity and a second position wherein the distal tip is spaced distally from the proximal base, the advancing step including moving the proximal base and the distal tip to the second position;

moving the distal tip and the proximal base, relative to one another, to the first position, thereby capturing tissue forming vessel walls between the artery and the vein between the proximal-facing surface and the distal-facing surface;

applying heat to the captured tissue with the catheter to ablate the tissue and form an anastomosis between the artery and the vein; and disabling venous valves to permit retrograde venous flow of arterial blood.

15. The method as recited in claim 14, and further comprising inflating a balloon adjacent to the needle to seat the needle against the wall of the vein and to push the stabilizing element around the artery.

16. The method recited in claim 15, wherein the balloon and stabilizing element are disposed on opposite sides of the catheter.

17. The method recited in claim 14, wherein the stabilizing element comprises a pair of arms extending at an angle with respect to each other, the needle extending between the arms when the stabilizing element is deployed and the needle is inserted into the vein.

\* \* \* \* \*